(12) United States Patent
Vaidya

(10) Patent No.: US 11,247,064 B2
(45) Date of Patent: Feb. 15, 2022

(54) TRANSCRANIAL MAGNETIC STIMULATION COIL ALIGNMENT APPARATUS

(71) Applicant: United States Government as Represented by the Department of Veterans Affairs, Washington, DC (US)

(72) Inventor: Punit Vaidya, Cleveland, OH (US)

(73) Assignee: United States Government as Represented by the Department of Veterans Affairs, Washington, DC (US)

(*) Notice: Subject to any disclaimer, the term of this patent is extended or adjusted under 35 U.S.C. 154(b) by 0 days.

(21) Appl. No.: 16/927,666

(22) Filed: Jul. 13, 2020

(65) Prior Publication Data
US 2021/0008382 A1     Jan. 14, 2021

Related U.S. Application Data

(60) Provisional application No. 62/873,013, filed on Jul. 11, 2019.

(51) Int. Cl.
*A61N 2/02* (2006.01)
*A61N 2/00* (2006.01)

(52) U.S. Cl.
CPC .............. *A61N 2/006* (2013.01); *A61N 2/02* (2013.01)

(58) Field of Classification Search
CPC .................................. A61N 2/006; A61N 2/02
See application file for complete search history.

(56) References Cited

U.S. PATENT DOCUMENTS

| | | |
|---|---|---|
| 2007/0260107 A1 | 11/2007 | Mishelevich et al. |
| 2014/0371515 A1 | 12/2014 | John |
| 2016/0354035 A1 | 12/2016 | Reihl et al. |
| 2018/0154165 A1 | 6/2018 | Schneider |
| 2019/0192874 A1 | 6/2019 | Shukla |

OTHER PUBLICATIONS

International Search Report and Written Opinion issued in related application No. PCT/US2020/041818 dated Oct. 7, 2020.

*Primary Examiner* — Christine H Matthews
(74) *Attorney, Agent, or Firm* — Ballard Spahr LLP

(57) ABSTRACT

An apparatus comprises a transcranial magnetic stimulation coil having a central axis and an array of electrical contacts. The array of electrical contacts can be configured to contact a conductor on a target area of a target surface. Processing circuitry can be configured to detect an engagement between the conductor and at least two electrical contacts of the array of electrical contacts. A plurality of range sensors can be spaced from the central axis of the transcranial magnetic simulation coil. A display can be configured to display a location corresponding to the engagement between the conductor and the at least two electrical contacts, a distance between each range sensor and the target surface, and a rotation of a coil with respect to a reference angle.

18 Claims, 16 Drawing Sheets

TRANSCRANIAL MAGNETIC STIMULATION COIL ALIGNMENT APPARATUS

CROSS REFERENCE TO RELATED APPLICATION

This application is a continuation of U.S. Application No. 62/873,013 filed Jul. 11, 2019, which is hereby incorporated by reference in its entirety.

BACKGROUND

Transcranial Magnetic Stimulation (TMS) is a brain stimulation methodology that uses high intensity pulsed magnetic fields via an electromagnetic coil that is placed over targeted areas of a patient's head to painlessly and non-invasively stimulate focal areas of the cortex for diagnostic or therapeutic purposes (such as for the treatment of medication-resistant major depressive disorder). Referring to FIG. 1, in clinical practice, the coil's windings are shaped in a figure-eight. Compared to a circular shaped coil, the figure-eight configuration allows for more focused stimulation of the underlying cortex, with intensity of stimulation being strongest directly under the center of the coil and projecting perpendicularly to the plane of the coil.

Because the induced electrical activity from TMS pulses is highly focused and decays very rapidly with distance from the center of the coil, proper contact with the target and coil orientation in 3-dimensional space with respect to the patient's head are critical for optimal stimulation. Several independent aspects of coil positioning can influence efficiency of stimulation. For example, small coil-to-head gaps can result in marked reduction of stimulation intensity at the cortex, and by consequence, can reduce clinical efficacy. Similarly, the TMS coil should ideally be tangential to the patient's scalp. If the TMS coil is making contact with the scalp but not centered directly over the desired target or in a tangential orientation, efficacy may also be compromised. Additionally, the angle of the coil, with respect to the mid-sagittal plane of the head, can influence cortical response to TMS. An angle of 45 degrees is generally considered optimal for cortical stimulation.

The technique of neuronavigation is one solution to improve accuracy and reliability of TMS coil placement. Neuronavigation systems, such as that developed by Rogue Research Inc., entails a complex imaging and computational system with multiple cameras and optical trackers attached to the coil and the patient's head. The system creates a 3-dimensional reconstruction of the coil location and orientation over an MRI image of the patient's brain. Such a technique is typically reserved for research purposes, as it is costly, time-intensive, and not practical for routine clinical application. Thus, in clinical practice, visual approximation is most commonly used to place the TMS coil and is the technique employed in 6 of the 7 devices FDA-approved for the treatment of major depression (the other being a neuro-navigation system). This method is crude since it does not provide objective confirmation of proper coil placement or contact with the target, is prone to errors, and can compromise clinical efficacy. Referring to FIG. 3, many of the methods for TMS coil placement rely on a cap, resembling a swimmer's cap, that is fit snuggly over the patient's head. The target is marked on the cap, and the coil is centered over the target at the start of each treatment. However, due to the dimensions of the coil, once placed on the head, the target marking and center of the underside of the coil are occluded from visual inspection, so the location of the edge of the coil is marked on the cap. As the coil is flat, the projection of this edge on the curved surface of the head is inherent to errors from visual parallax, both at times of target demarcation and each time the coil is placed for subsequent treatments. Additionally, one must rely on visual estimation to determine if the coil is tangentially placed on the scalp and at 45 degrees from the mid-sagittal plane, as shown in FIG. 2. All of these potential sources of error can result in significant variability in coil placement between TMS operators and over repeated treatment session and, thus, may result in suboptimal therapeutic response.

For the treatment of major depression, the TMS coil must be properly positioned for the duration of the treatment, which typically lasts 19-38 minutes. Conventional devices do not provide continuous feedback to the operator regarding proper coil placement. Small movements of the patient's head (for example, by head turning, coughing, sneezing, or shifting in the treatment chair) may change the coil-to-target placement and thereby impact clinical efficacy. Thus, it is important that feedback on coil positioning is provided to the TMS operator not only prior to the start of each treatment session, but continuously over the duration of each treatment session.

One attempt to aid in TMS coil placement uses a touch-sensitive film located under the surface of the coil to detect if scalp contact is maintained. However, there are limitations to this technique, as this method can indicate only that the coil is making contact with the head, but does not specify if the coil is centered over the target. For example, it would not be uncommon for the patient to slide down the treatment chair or turn his/her head by a small but clinically significant distance during the duration of the treatment. The operator may be informed of lack of scalp contact and reposition the coil, but it is possible that the coil will no longer be centered over the target, as the system provides no such objective, positional feedback. Additionally, this method is susceptible to error as the coil is aligned with respect to ruler markings on the headrest of the chair, rather than aligned directly to the patient's head.

SUMMARY

Described herein, in various aspects, is an apparatus comprising a transcranial magnetic stimulation coil having a central axis and an array of electrical contacts, wherein the array of electrical contacts is configured to contact a conductor on a target area of a target surface. Processing circuitry can be configured to detect an engagement between the conductor and at least two electrical contacts of the array of electrical contacts. A plurality of range sensors can be spaced from the central axis of the transcranial magnetic simulation coil. A display can be configured to display a location corresponding to the engagement between the conductor and the at least two electrical contacts, and a distance between each range sensor and the target surface.

The apparatus can further comprise a first light emitting device configured to display a first line, and a second light emitting device configured to display a second line.

Each of the first light emitting device and the second light emitting device can be a laser diode.

The apparatus can further comprise at least one orientation sensor, wherein the processing circuitry is configured to determine an orientation of the transcranial magnetic stimulation coil apparatus based on data from the at least one orientation sensor.

The at least one orientation sensor can comprise a three-axis accelerometer, a three-axis gyroscope, and a three-axis magnetometer.

The apparatus can further comprise memory. The processing circuitry can be configured to store in the memory a reference orientation based on at least one measurement from the at least one orientation sensor. The processor can be configured to determine a relative orientation of the TMS coil with respect to the reference orientation. The display can be further configured to display the relative orientation of the TMS coil apparatus with respect to the reference orientation.

Each electrical contact can be evenly spaced from each respective adjacent electrical contact.

The plurality of range sensors can comprise at least two range sensors.

The apparatus can further comprise a wireless transmitter that is configured to transmit data captured by the apparatus to a receiver operably coupled to a remote display.

The array of electrical contacts can be centered with respect to the central axis, and the plurality of range sensors can be equally spaced from the central axis.

The array can comprise at least two rows and at least two columns.

The apparatus can further comprise a second orientation sensor, wherein the processing circuitry is configured to compare orientation data from the second orientation sensor to orientation data from the at least one orientation sensor.

An apparatus can comprise a housing configured to couple to a transcranial magnetic stimulation coil device and an array of electrical contacts, wherein the array of electrical contacts is configured to contact a conductor on a target area of a target surface. Processing circuitry can be configured to detect an engagement between the conductor and at least two electrical contacts of the array of electrical contacts. A plurality of range sensors can be disposed around a circumference of the array of electrical contacts.

The apparatus can further comprise a display that is configured to display: a location corresponding to the engagement between the conductor and the at least two electrical contacts, and a distance between each range sensor and the target surface.

The apparatus can further comprise at least one orientation sensor, wherein the processing circuitry is configured to determine an orientation of the transcranial magnetic stimulation coil apparatus based on data from the at least one orientation sensor, and memory. The processing circuitry can be configured to store in the memory a reference orientation based on at least one measurement from at least one orientation sensor. The processor can be configured to determine a relative orientation of the TMS coil with respect to the reference orientation. The display can be further configured to display the relative orientation of the TMS coil apparatus with respect to the reference orientation.

The apparatus can further comprise a wireless transmitter that is configured to transmit data captured from the apparatus to a receiver operably coupled to a remote display.

A system can comprise an apparatus comprising a transcranial magnetic stimulation coil having a central axis and an array of electrical contacts, wherein the array of electrical contacts is configured to contact a conductor on a target area of a target surface. Processing circuitry can be configured to detect an engagement between the conductor and at least two electrical contacts of the array of electrical contacts. A plurality of range sensors can be spaced from the central axis of the transcranial magnetic simulation coil. The apparatus can further comprise wireless transmitter. The system can further comprise a remote display comprising a receiver and that is configured to display a location corresponding to the engagement between the conductor and the at least two electrical contacts and a distance between each range sensor and the target surface. The wireless transmitter can be configured to transmit data captured by the apparatus to the receiver of the remote display.

The apparatus can further comprise at least one orientation sensor. The processing circuitry can be configured to determine an orientation of the transcranial magnetic stimulation coil apparatus based on data from the at least one orientation sensor. The remote display can comprise memory. The processing circuitry can be configured to store a reference orientation based on at least one measurement from the at least one orientation sensor. The processor can be configured to determine a relative orientation of the TMS coil with respect to the reference orientation. The display can be further configured to display the relative orientation of the TMS coil apparatus with respect to the reference orientation.

A method can comprise: receiving a signal corresponding to an engagement between a conductor and at least a first electrical contact and a second electrical contact of a plurality of electrical contacts; determining, based on the signal, a contact location, wherein the contact location is a position between the first electrical contact and the second electrical contact; receiving a distance measurement from each of a plurality of range sensors; displaying the contact location on a display; and displaying the distance measurement from each of the plurality of range sensors on the display.

Displaying the contact location on the display can comprise graphically displaying the contact location as a radial offset from a center point.

Displaying the distance measurement from each of the plurality of range sensors on the display can comprise graphically displaying the distance measurement from each of the plurality of range sensors as a radius from a center point.

The method can further comprise calculating a vector as a function of each distance measurement from each of the plurality of range sensors and displaying the vector on the display.

The method can further comprise transmitting the signal and the contact location to the display, wherein the display is a remote display.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein:

FIGS. 9A-9C illustrate the example display with a vector showing the range sensor data from the TMS coil apparatus of FIG. 4;

DETAILED DESCRIPTION

Figure 1:
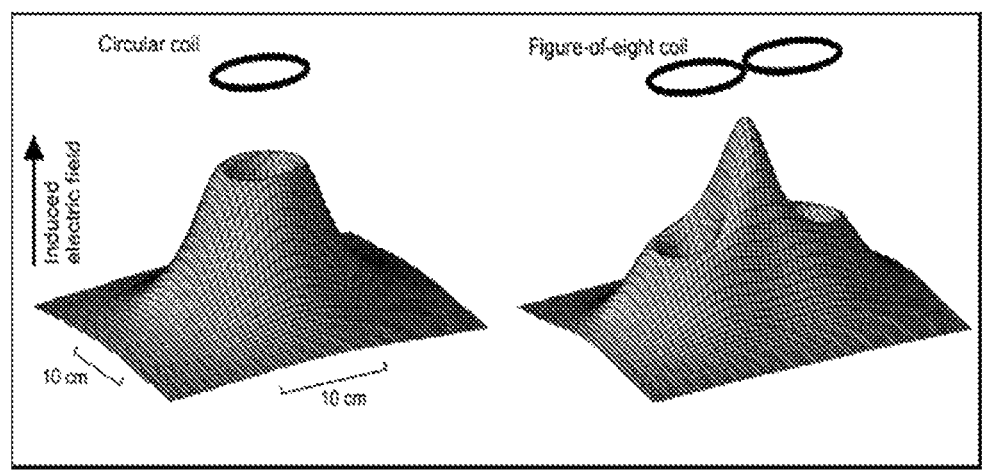
FIG. 1 is an example graph of strength of electric field inducted by a circular (left) and figure-eight-shaped coil (right).
Figure 2:
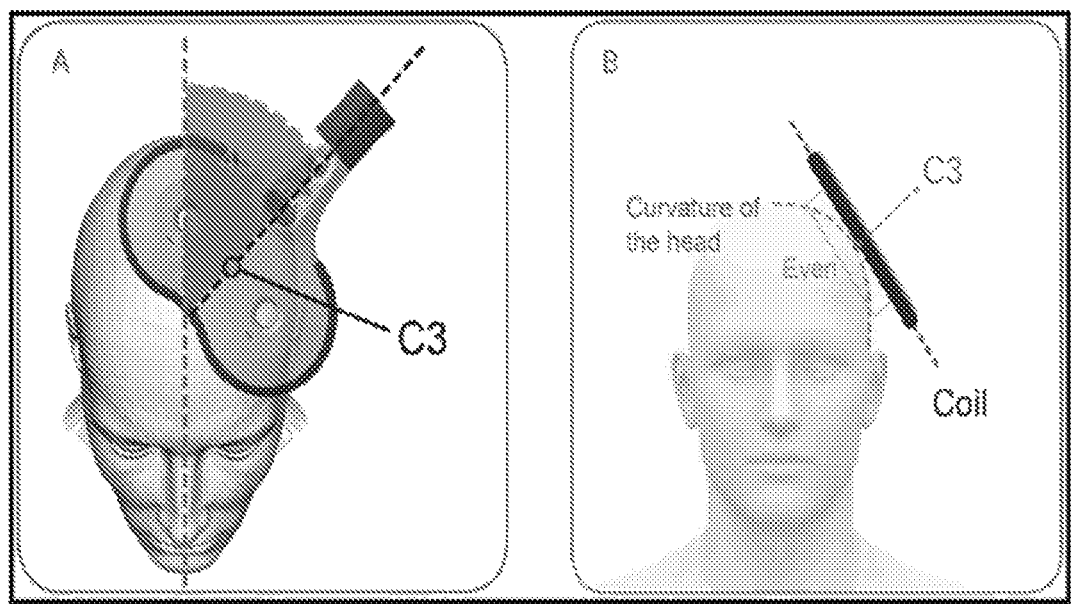
FIG. 2 is an example pair of diagrams indicating ideal placement and orientation of a TMS coil.
Figure 3:
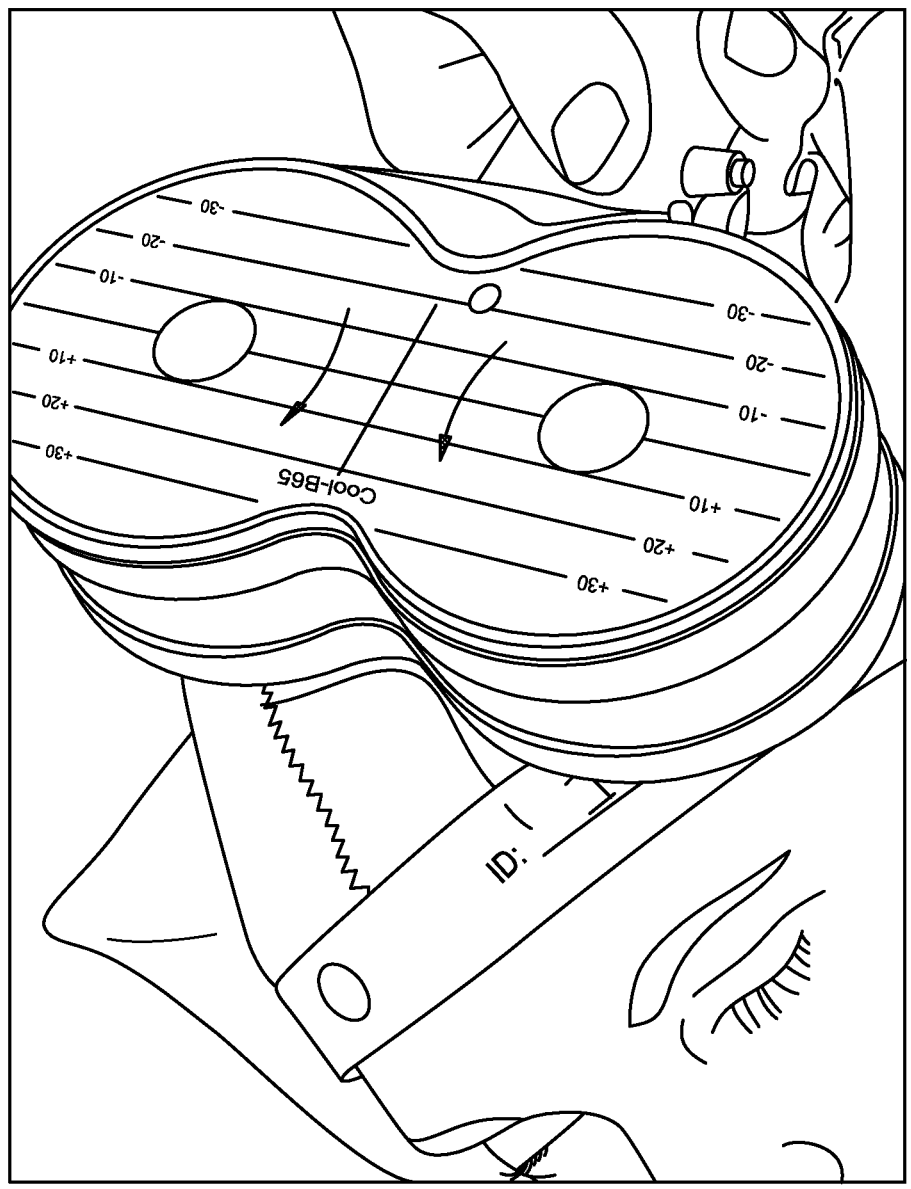
FIG. 3 is an example image of a conventional TMS coil on a patient.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" include plural referents unless the context clearly dictates otherwise. For example, use of the term "a sensor" can refer to one or more of such sensors, and so forth.

All technical and scientific terms used herein have the same meaning as commonly understood to one of ordinary skill in the art to which this invention belongs unless clearly indicated otherwise.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of" For example, "at least one of A, B and C" explicitly includes only A, only B, only C, and combinations of each.

Ranges can be expressed herein as from "approximately" one particular value, and/or to "approximately" another particular value. When such a range is expressed, another aspect includes from the one particular value and/or to the other particular value. Similarly, when values are expressed as approximations, by use of the antecedent "approximately," it will be understood that the particular value forms another aspect. It will be further understood that the endpoints of each of the ranges are significant both in relation to the other endpoint, and independently of the other endpoint. Optionally, in some aspects, when values are approximated by use of the antecedent "approximately," it is contemplated that values within up to 15%, up to 10%, up to 5%, or up to 1% (above or below) of the particularly stated value can be included within the scope of those aspects.

The word "or" as used herein means any one member of a particular list and also includes any combination of members of that list.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

Figure 4:
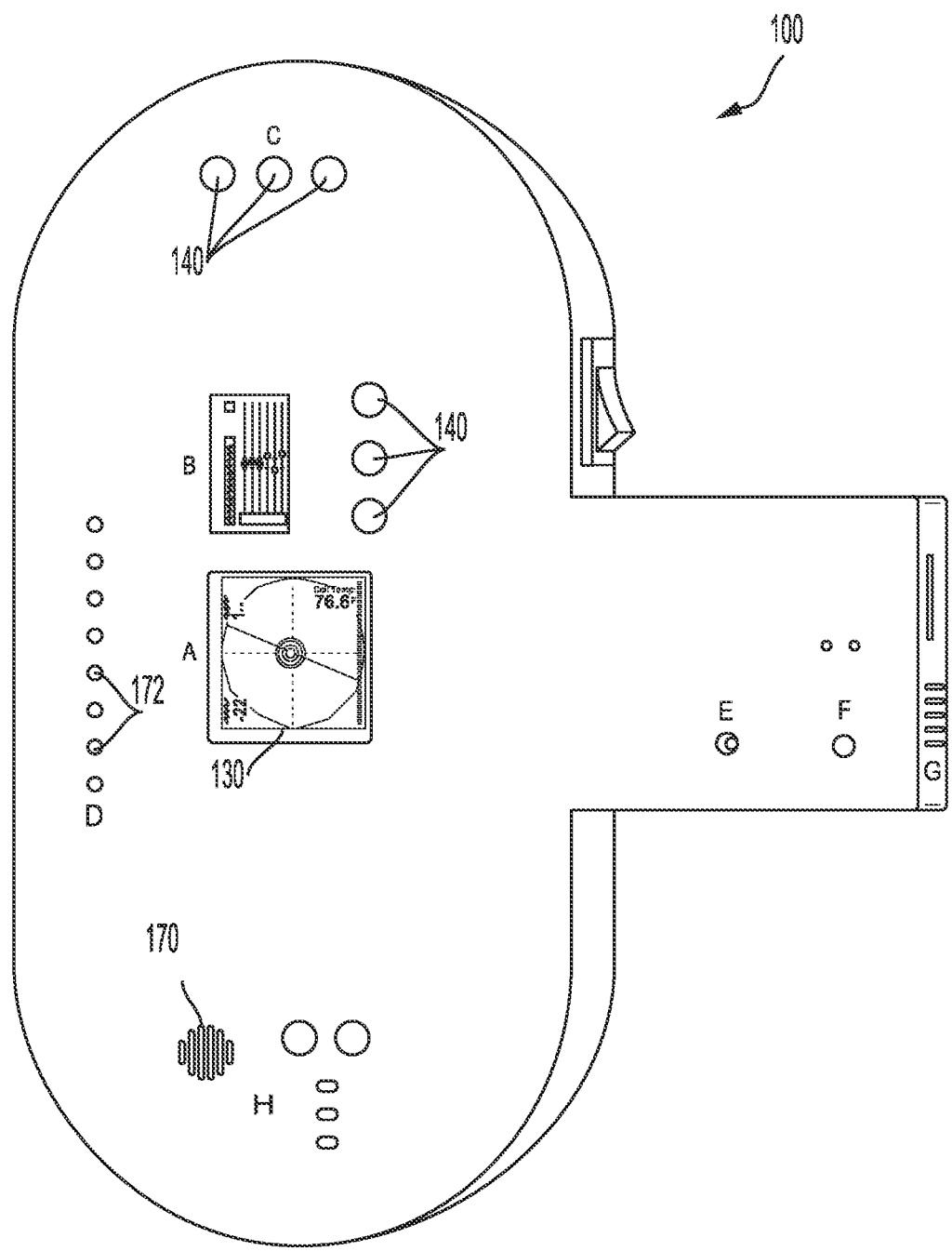
FIG. 4 is an example top view of a TMS coil apparatus in accordance with embodiments disclosed herein.
Figure 5:
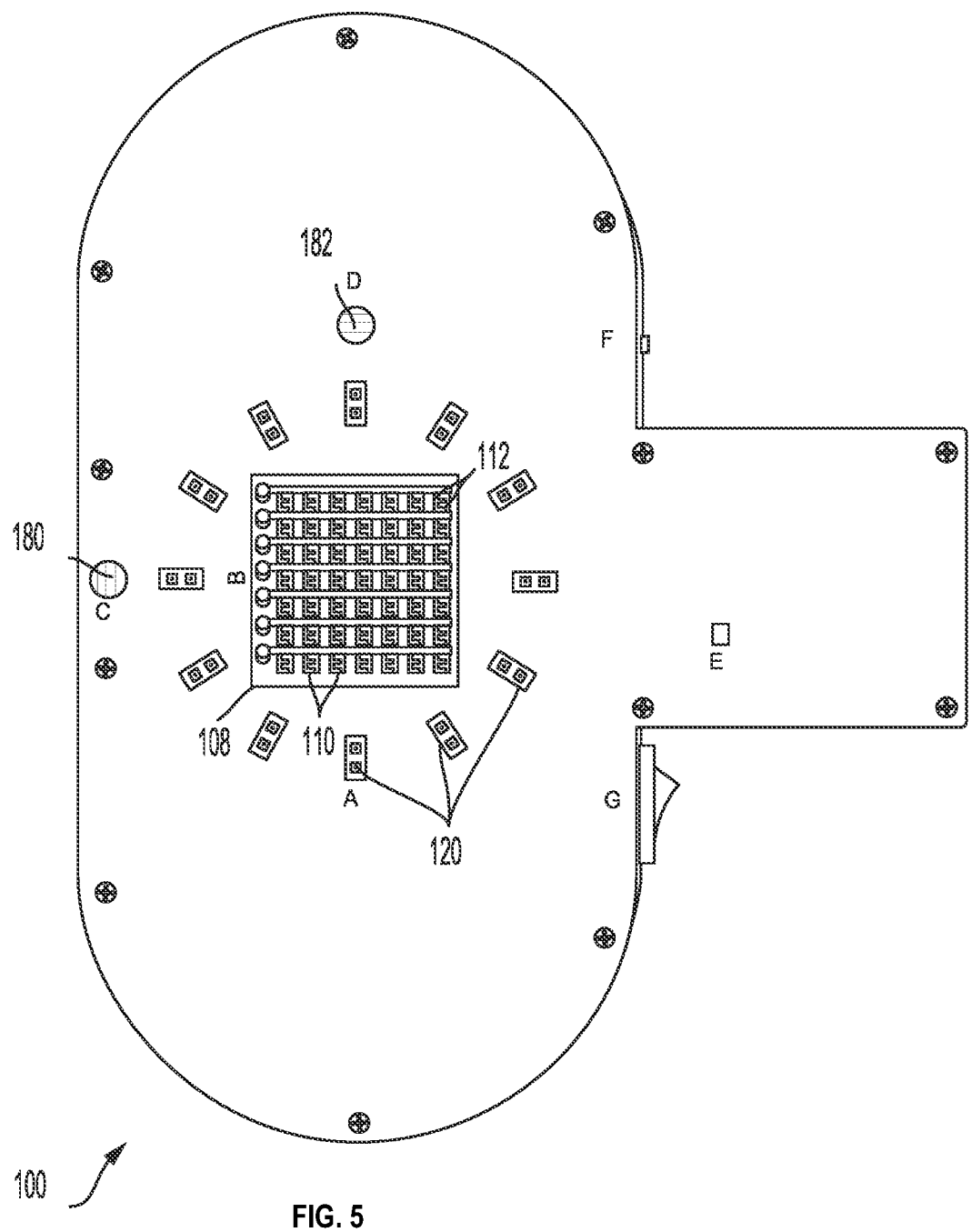
FIG. 5 is an example bottom view of the TMS coil apparatus of FIG. 4.

Disclosed herein, in various aspects and with reference to FIGS. 4 and 5, is a TMS coil apparatus 100. In some embodiments, the TMS coil apparatus 100 can comprise a figure-eight coil pattern. In further embodiments, the TMS coil apparatus 100 can comprise a circular coil pattern, which can be beneficial in stimulating peripheral nerves. In still further embodiments, the TMS coil apparatus 100 can comprise various other coil patterns, such as an h-coil pattern. The TMS coil can be configured to generate an electromagnetic field along an axis 90 (FIG. 1) to selectively stimulate a target area of a patient's brain.

The TMS coil apparatus 100 can comprise an array 108 of contact pads 110. Each contact pad 110 can comprise an array of spaced tracings pairs 112. The tracings in each of the spaced tracing pairs 112 can be separated by a thin strip of non-conductive material. Accordingly, when the spaced tracing pairs 112 simultaneously contact a conductor, the conductor can bridge the thin strip of non-conductive material to electrically couple the pair of spaced tracings 112. A controller (e.g., a computing device 1001, as further discussed herein), can detect when each pair of spaced tracings 112 are electrically coupled. In some embodiments, the array 108 can comprise a 7×7 matrix of contact pads 110 that are arranged to cover a two inch by two inch square area. The array 108 can be centered with the axis of the TMS coil so that the array 108 can help align the coil with the target area, as further discussed herein.

Figure 6A:
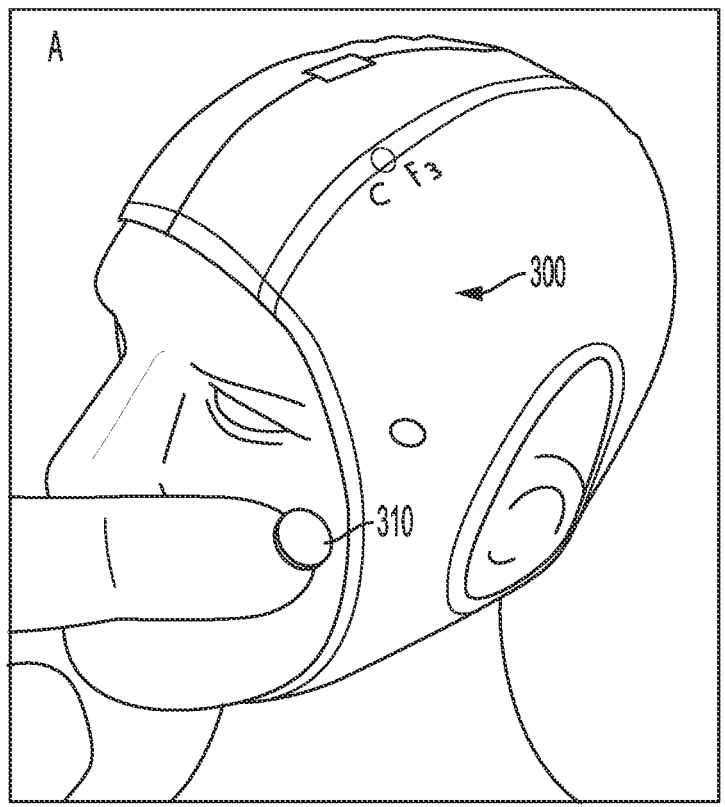
FIGS. 6A and 6B illustrate example images of a cap and a target marker for use with the TMS coil apparatus of FIG. 4.
Figure 6B:
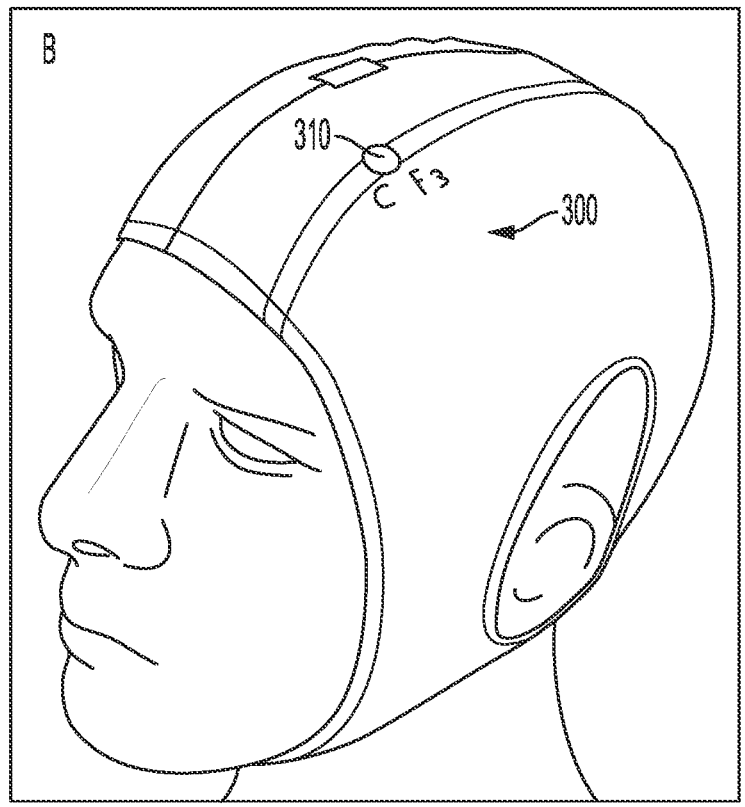

Referring also to FIGS. 6A and 6B, the TMS coil apparatus 100 can cooperate with a cap 300 that is placed over the patient's head. The cap 300 can be thin and snugly fit on the patient. The cap 300 can be positioned with respect to fixed features on the patient's head (e.g., eyes and nose) so that the cap 300 can be repeatedly placed on the patient's head in the same position. Optionally, the cap 300 can be marked with respect to the fixed features on the patient's head so that the cap 300 can be repeatedly placed on the patient's head in the same alignment. A target marker 310 can be placed on the cap 300 at the intended area of stimulation. The target marker 310 can be circular (e.g., ½ centimeter in diameter) and thin to minimize spacing of the TMS coil from the patient's head. The target marker 310 can be a conductor that can have an adhesive backing.

The TMS coil apparatus 100 can be placed against the patient's head so that the array 108 of contact pads 110 rests against the target marker 310. The target marker 310 can electrically couple each of the spaced tracing pairs 112 that target marker 310 simultaneously contacts, thereby closing a circuit that extends between each said spaced tracing pair. The controller can continuously or intermittently poll to detect which pad(s) 110 in the array 108 is/are contacting the target marker 310. In this way, the controller can determine the position of the TMS coil apparatus 100 with respect to the target marker 310 and, thus, the intended area of stimulation.

Figure 7A:
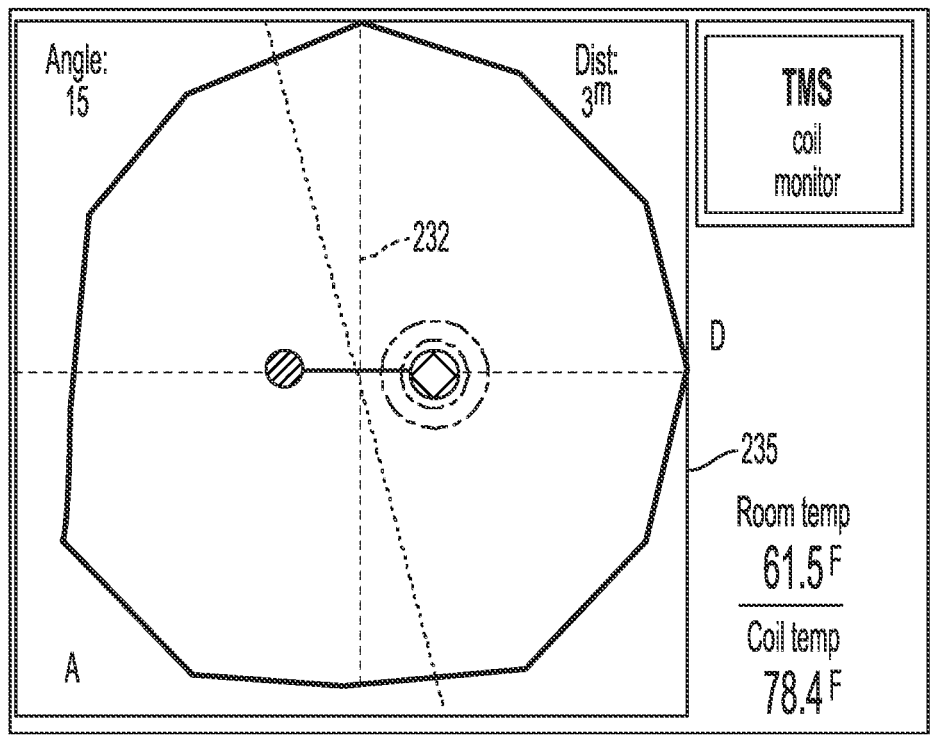
FIGS. 7A-7C illustrate an example display indicating location of the TMS coil apparatus of FIG. 4 with respect to the target marker of FIG. 6A.
Figure 7B:
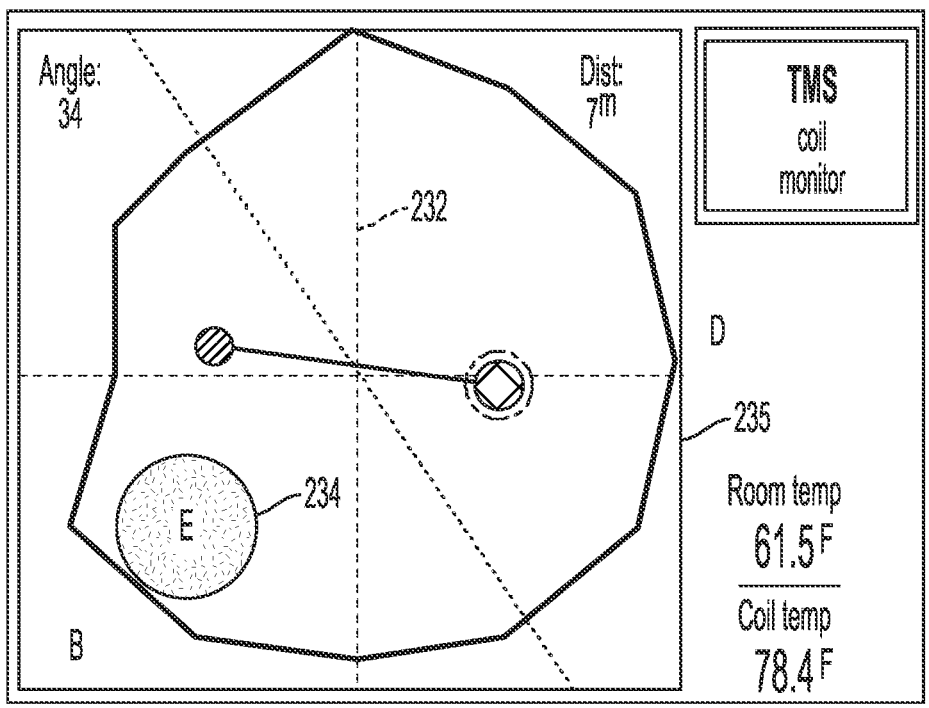
Figure 7C:
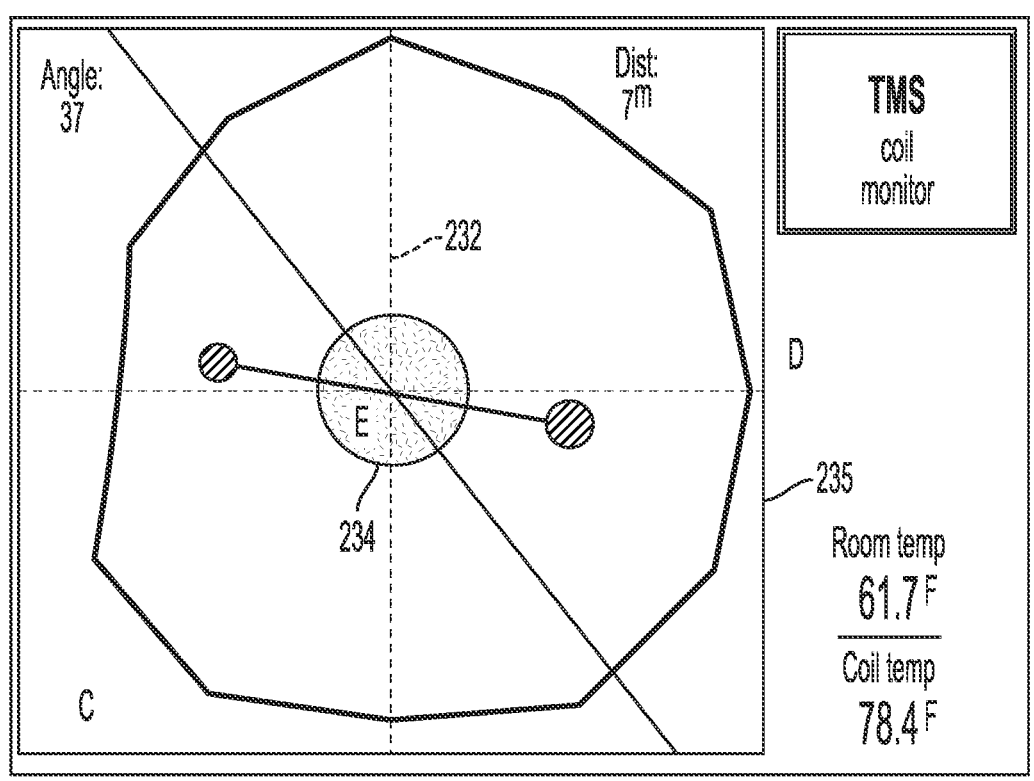

Referring also to FIGS. 7A-7C, the TMS coil apparatus 100 can comprise a display 130 such as, for example, an LCD screen. The display 130 can show, based on which contact pads 110, if any, are contacting the target marker 310, the position of the array 108 with respect to the target marker 310. In at least one embodiment, the display 130 can show a spot 234 in relation to a crosshair 232 that corresponds to which contact pads 110, if any, are in contact with the target marker. For example, in FIG. 7A, the display 130 does not show a spot 234, indicating that no contacts pads 110 in the array 108 are contacting the target marker 310. In FIG. 7B, the spot 234 is spaced from the center of the crosshair 232, indicating that the TMS coil apparatus 100 is off-center. FIG. 7C illustrates the spot 234 in the center of the crosshair 232, indicating that the axis of the TMS coil apparatus 100 is centered over the target marker 310 and, thus, the target area. In this way, an operator can receive feedback from the display 130 and move the TMS coil apparatus until the TMS coil is properly positioned with respect to the target area. Optionally, the display 130 can show a border 235 that changes color (e.g., from red to green) when the TMS coil apparatus 100 contacts the target marker 310.

It should be understood that the display 130 can show an average position of the contact pads 110 that are contacting the target marker 310. For example, if two contact pads 110 are touching the target marker 310 simultaneously, the display 130 can show the spot 234 in a location with respect to the crosshairs 232 corresponding to the position between the two contact pads 110. As another example, if six contact pads 110 arranged in a 2×3 grid are touching, the display can display the location corresponding to the position of the 2×3 grid's center.

Referring to FIG. 5, the TMS coil apparatus 100 can further comprise a system for tangentially aligning the TMS coil apparatus 100 with respect to the patient's head. The TMS coil apparatus 100 can comprise a plurality of range sensors 120 spaced in a circular pattern that is centered about the axis of the TMS coil. The plurality of range sensors 120 can be time-of-flight sensors that can send laser pulses and measure the time for each pulse to reflect off a surface and return to a detector. The plurality of range sensors 120 can be equally spaced from the axis of the TMS coil. Each range sensor of the plurality of range sensors 120 can each detect a respective distance to the patient's head. The plurality of range sensors 120 can capture distance measurements, and the TMS device can represent the distance measurements as a vector having the measured distance as the vector's magnitude and an angular value defined as an azimuthal angle of the range sensor about the TMS coil's axis. The TMS coil apparatus 100 can be considered tangentially oriented with respect to a patient's head when the sum of all of the vectors is zero.

Figure 8A:
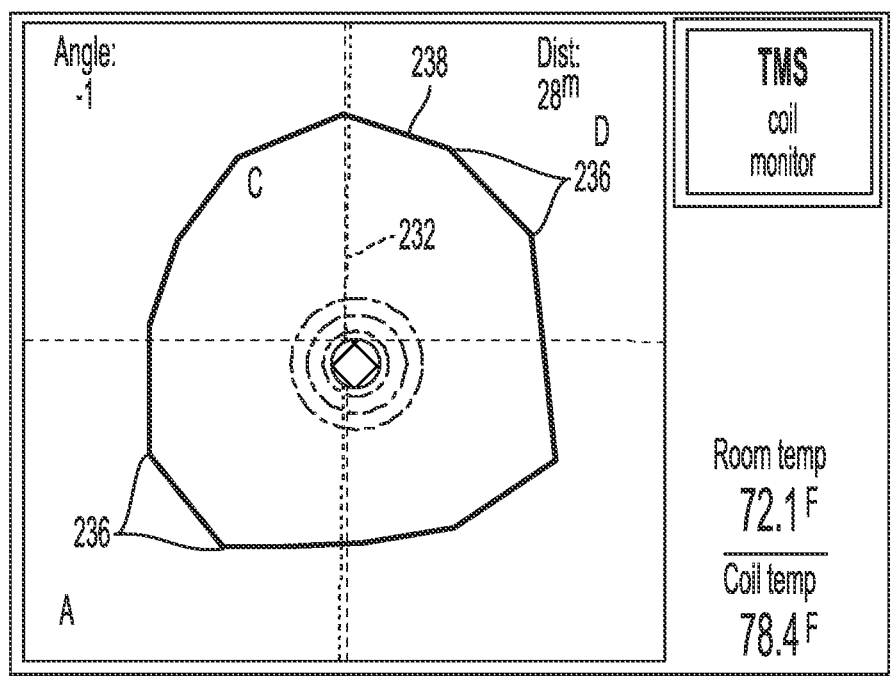
FIGS. 8A-8B illustrate an example graphical display of range sensor data from the TMS coil apparatus of FIG. 4.
Figure 8B:
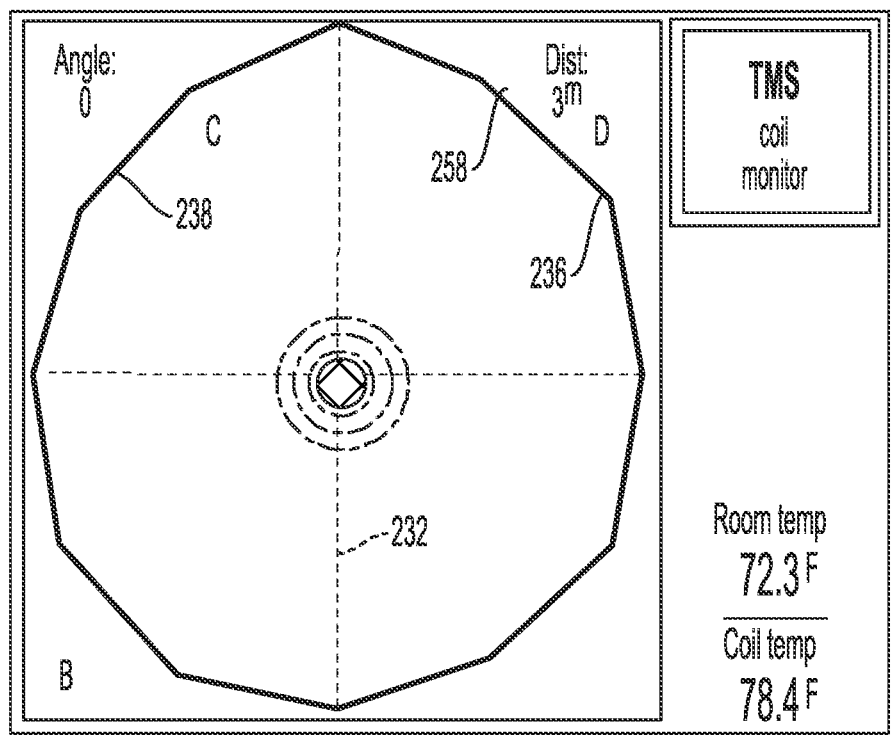

Referring also to FIGS. 8A and 8B, the display 130 can display the respective distances of each range sensor of the plurality of range sensors 120 as a vertex 236 of a polygon 238, wherein the distance from the center of the crosshair 232 corresponds to the distance to the patient's head. Optionally, the distance from the center of the crosshair 232 to each vertex can increase as the respective range sensor of the plurality of range sensors 120 approaches the patient's head. Accordingly, an operator can orient the TMS coil apparatus 100 to center the polygon 238 with the center of the crosshair 232, indicating that the TMS coil apparatus 100 is generally tangential to the patient's head.

Figure 9A:
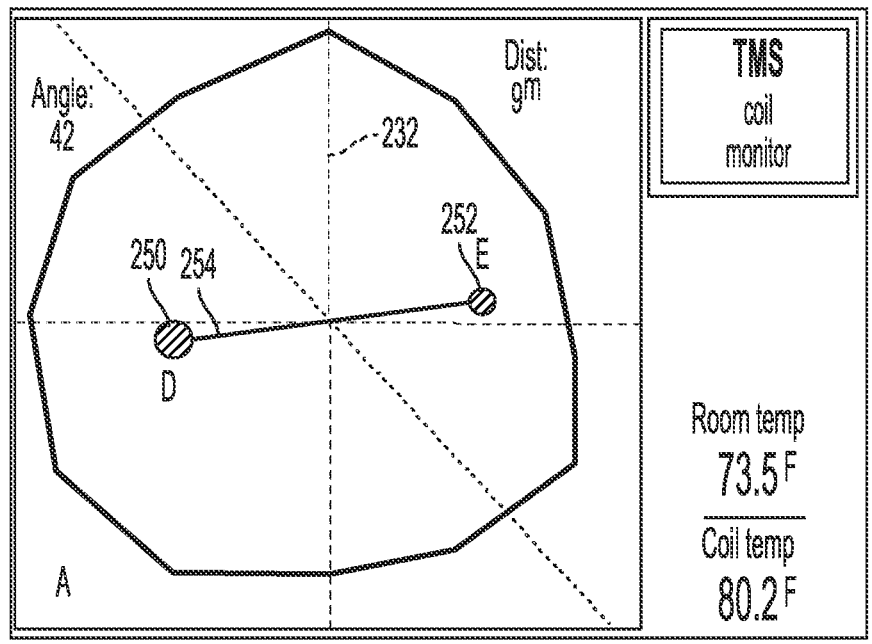
Figure 9B:
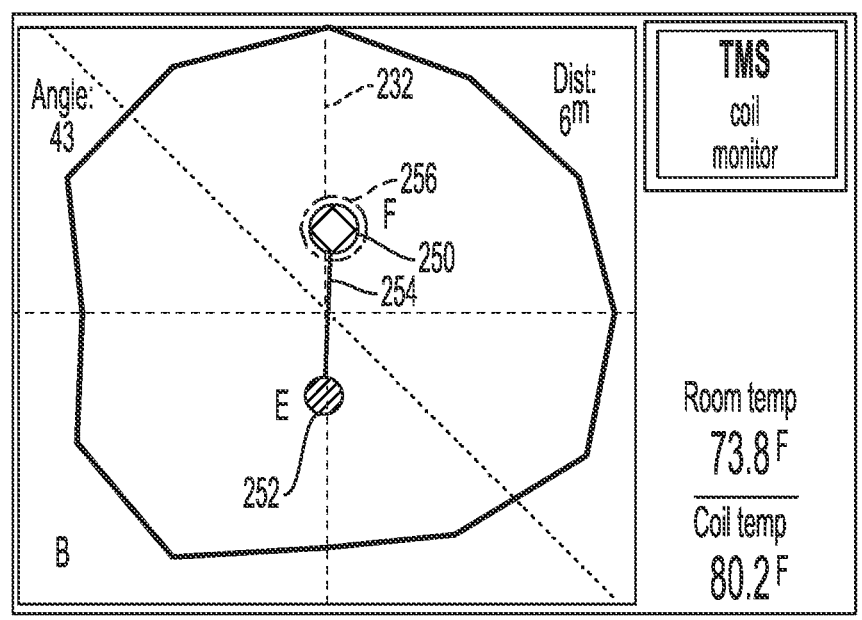

Further, referring to FIGS. 9A-9C the controller can aggregate data from the range sensors 120 to provide an indication to the operator as to how close the TMS coil apparatus 100 is to tangential to the patient's head as well as how the TMS coil apparatus 100 can be adjusted to further improve its tangential orientation. For example, the controller can compute an average of the vectors corresponding to each range sensor's the distance to the patient's head and the range sensor's respective azimuthal angle about the TMS coil's axis. For example, the controller can compute a vector sum based on distance measurements and the position of each range sensor of the plurality of range sensors 120. The relative distances (e.g., vectors) may be compared to determined an angle of the coil with respect to the head. For example, if a range sensor located at the 12 o'clock position is close to the head than a range sensor the 6 o'clock position, it may be determined that the coil is tiled with respect to the head. The display 130 can then show a first spot 250 indicating a vector based on the sum of the range sensors' vectors. The first spot 250 can be spaced from the center of the crosshair 232 showing in a direction toward which the TMS coil apparatus 100 should be tilted to improve the tangential orientation. The display 130 can further show a complementary second spot 252 equally spaced in the opposite direction from the center of the crosshair 232 and a line 254 between the first spot 250 and the second spot 252, showing a visible vector further indicating the direction that the TMS coil apparatus 100 should be tilted. The display 130 can optionally show the average distance 258 from the range sensors 120 to the patient's head.

As the first spot 250 and the second spot 252 converge, it should be understood that they will overlap so that the relative direction from the crosshair's center may be difficult to ascertain. Accordingly, as the first spot 250 nears the crosshair's center, the display 130 can show an increasing number of concentric rings 256 around the first spot 250. For example, zero concentric rings 256 (FIG. 9A) can show that the TMS coil apparatus 100 is far from tangential alignment, one concentric ring (FIG. 9B) can indicate better tangential alignment, two concentric rings (not shown) can indicate still better tangential alignment, and three concentric rings (FIG. 9C) can indicate optimal tangential alignment.

Optionally, one or more buttons 140 can toggle between what is shown on the display. Accordingly, in at least one embodiment, the operator can switch between the display showing the spot 234 and the first and second spots 250, 252. In further embodiments, the display can show all of spot 234 and first and second spots 250, 252 simultaneously.

Referring to FIGS. 5, 10A-10C, and 13, the TMS coil apparatus 100 can further comprise one or more laser guides and an absolute 3-axis orientation sensing system. According to some aspects, the TMS coil apparatus can comprise a vertical axis laser 180 and a horizontal axis laser 182 that can each comprise a laser diode. The vertical axis laser 180 can emit a first laser line 280 that is aligned with the TMS coil's axis, and the horizontal laser 182 can emit a second laser line 282 that is perpendicular to the first laser line 280 and is aligned with the TMS coil's axis. Accordingly, the first and second laser lines 280, 282 can intersect at the stimulation site. The lasers lines can optionally be turned on and off via a button 140.

The TMS coil apparatus 100 can comprise orientation sensors 150 such as, for example, a three-axis accelerometer 152, a three-axis gyroscope 154, and/or a three-axis magnetometer 156. The three-axis accelerometer 152 can optionally comprise a plurality of accelerometers that are oriented with respect to each other to sense orientation along their respective axes so that their cumulative orientation data can cooperate to provide the orientation of the three-axis accelerometer 152 in all three dimensions.

The operator can align the first laser line 182 with a vertical line on the cap 300. Once the laser line 282 and the vertical line are aligned (corresponding with the TMS coil being at a zero-degree alignment with respect to the mid-sagittal plane), the operator can then actuate a button 140 that causes the TMS coil apparatus 100 to store the three-dimensional orientation information that can be used as a reference orientation. Accordingly, as it can be desirable to orient the TMS coil apparatus 100 at forty-five degrees with respect to the mid-sagittal plane, the TMS coil apparatus 100 can be tilted forty-five degrees from the reference orientation with respect to the mid-sagittal plane for optimal results. The display 130 can show the TMS coil apparatus's orientation with respect to the reference orientation as a numerical display 290 and geometrically as a line 292 angled with respect to the crosshairs 232.

A reference orientation sensor module 320 can be secured to the patient, for example, as a component that is integral to the cap 300 or attached to the cap with a fastener such as hook and loop. The reference orientation sensor module 320 can comprise orientation sensors (e.g., accelerometers, gyroscopes, megnetometers, combinations thereof, and the like) and act as a reference for comparing movement of the TMS coil apparatus 100 with movement of the patient. In this way, after alignment, the operator can determine if movement of the TMS coil apparatus 100 corresponds with respective movement of the patient or if the TMS coil apparatus 100 has moved with respect to the patient. For example, if the reference orientation sensor module 320 detects that the patient moves his or her head five degrees about an axis, and the orientation sensors 150 detect that the TMS coil apparatus similarly rotates five degrees about the axis, it can be understood that the TMS coil apparatus is still likely in proper alignment with the target area. If, however, the orientation sensors 150 detect that TMS coil apparatus rotates five degrees about the axis, and the reference orientation sensor module 320 detects no movement, it can be understood that the TMS coil likely moved with respect to the patient and is no longer in proper alignment with the target area.

Figure 10A:
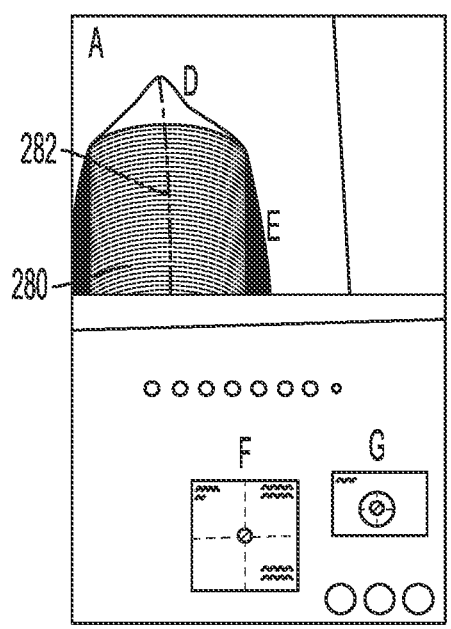
FIGS. 10A-10C illustrate example images showing steps for using alignment lasers and orientation sensors to align the TMS coil apparatus of FIG. 4.
Figure 10B:
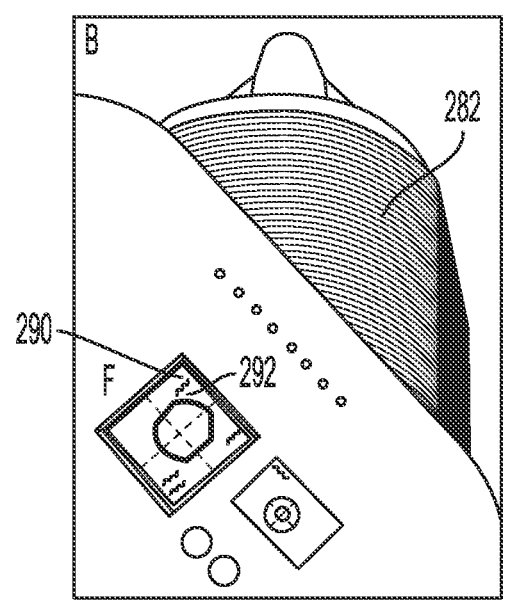
Figure 10C:
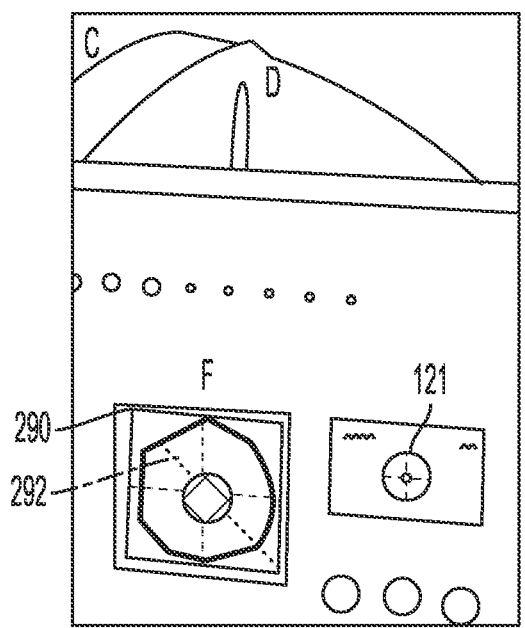
Figure 11:
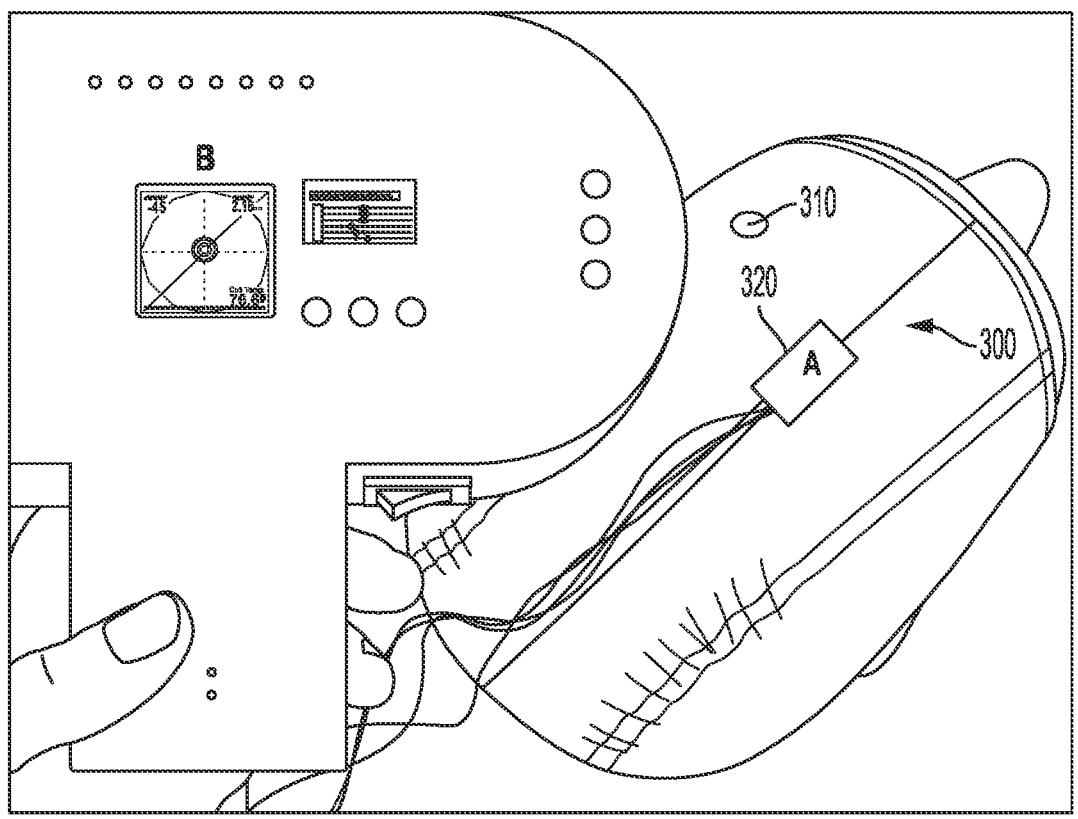
FIG. 11 illustrates an example image of dynamic reference orientation sensor that is attached to a patient for providing orientation data of the patient for comparison to orientation data from the TMS coil apparatus.
Figure 12:
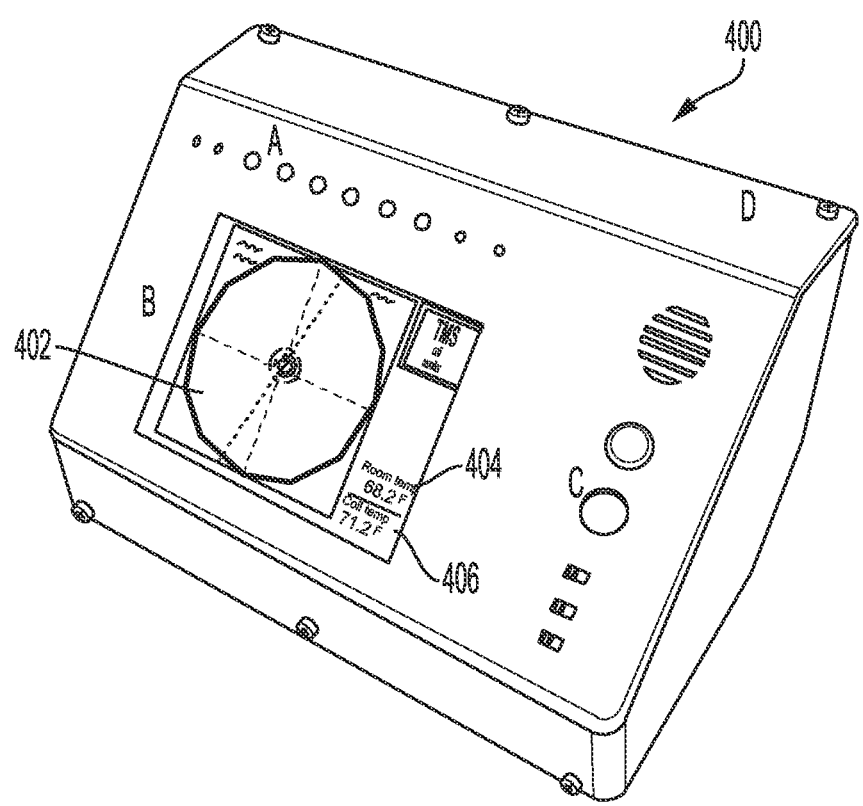
FIG. 12 illustrates an example image of a remote display for use with the TMS coil apparatus of FIG. 4.

Referring to FIG. 10C, optionally, a secondary display 121 can provide various information to the operator, including a virtual "bubble level" that can show orientation with respect to a pair of axes. The operator can optionally set the reference positions for said pair of axes. The virtual bubble level can be used for orienting the coil. In some embodiments, the virtual bubble levels can provide graphic representations of accelerometer data either in absolute readings or compared to a reference orientation. In further embodiments, the virtual bubble levels can provide graphic representation of a relationship between the TMS coil apparatus 100 and the reference orientation sensor module 320. In still further embodiments, the virtual bubble levels can illustrate orientation changes with respect to a treatment orientation—that is, with respect to orientation data captured at a previous time when the TMS coil apparatus 100 was positioned for a treatment.

It is common during TMS operations that the operator is several feet away from the patient so that the display 130 is not viewable to the operator. Moreover, TMS operations can typically take nineteen to thirty-eight minutes, during which the patient can move. Although the TMS coil apparatus 100 can be locked into place and secured by an articulated support arm that is commonly used in the art, small movements of the patient can result disrupted engagement of the target with the TMS coil apparatus 100, which can lead to less than optimal results. Accordingly, the TMS coil apparatus 100 can include a wireless transmitter in communication with a remote display 400 that can provide real-time positioning information that is similar to that of the display 130. For example, the remote display 400 can include an LED screen 402. The remote display 400 can show all of the same information as display 130, including the crosshair 232 and the spot 234, the polygon 238 and the first and second spots 150, 252, and line 254. The remote display 400 can further show the numerical display 290 the line 292 angled with respect to the crosshairs 232. Accordingly, the remote display 400 can show all of the information provided on the display 130. Moreover, the remote display 400 can show additional information, such as room temperature 404, which can contribute to coil overheating, and coil temperature 406.

Accordingly, the TMS coil apparatus 100, as disclosed herein enable an operator to align the TMS coil with the target. In particular, the TMS coil apparatus 100 can provide the operator with visual feedback (including the display 130, the vertical axis laser 180, and the horizontal axis laser 184) for properly aligning the TMS coil.

The TMS coil apparatus 100 and/or remote display 400 can further include a speaker 170 to give audio feedback to the operator. For example, the computing device 1001 can determine that the TMS coil apparatus has moved a threshold amount from its alignment with the target. In response, the TMS coil apparatus can provide audible feedback to the operator. Further, the TMS coil apparatus 100 and/or the remote display 400 can comprise alarm lights 172 (e.g., RGB LEDs). The alarm lights 172 can indicate various conditions (e.g., whether the TMS coil apparatus is centered on the target, tangential to the patient's head, and properly angled with respect to the mid-sagittal plane) based on, for example, which lights are lit, a number of lights that are lit, the intensity of the lights, and the color of the lights. The computing device 1001 can be programmed for providing feedback with the speaker 170 and alarm lights 172 upon various conditions. In some embodiments, the TMS coil apparatus 100 can have a coil temperature sensor 174. The speaker 170 and/or alarm lights 172 can provide an indication that the coil temperature has passed a threshold.

In various embodiments, the TMS coil apparatus can comprise a plurality of LEDs spaced circularly around the display 130 that can indicate (e.g., based on their colors, intensity, and on/off status). In various embodiments, the plurality of LEDs circularly spaced LEDs can indicate a direction that the TMS coil apparatus should be moved, how it should be tilted, and/or how it should be rotated. In an embodiment, based on the information from the sensors, specification instructions may be determined which may be displayed so as to aid in the placement of the coil. For example, an instruction such as "move coil left," or "tilt coil forward," or "turn coil clockwise," may be displayed. Such instructions may be conveyed via text, audio outputs, or visual displays such as graphical displays.

Figure 15:
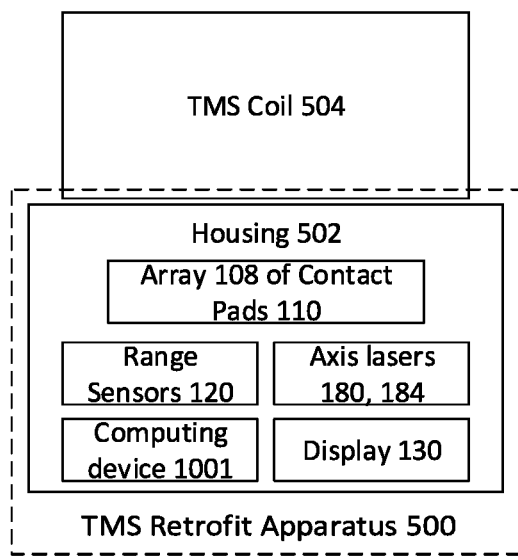
FIG. 15 illustrates an example schematic of a TMS coil retrofit apparatus.

Referring to FIG. 15, in some embodiments, components of the TMS coil apparatus 100 can be configured to retrofit a TMS coil 504. For example, in one embodiment, a TMS retrofit apparatus 500 can comprise a housing 502. The housing 502 can couple to the TMS coil 504 in a fixed location with respect to the TMS coil's stimulation axis. The housing 502 can be configured to removably attach to a TMS coil e.g., via clips or hook and loop fasteners. Preferably, the housing 502 can be configured to cause minimal additional spacing in the axial dimension from the patient's head. Accordingly, the housing 502 can comprise a thin material. The TMS retrofit apparatus 500 can comprise some or all of the features of the TMS coil apparatus 100, including, but not limited to: an array 108 of contact pads 110, a plurality of range sensors 120, vertical and horizontal axis lasers 180, 184, a computing device 1001, and a display 130 and/or other output devices.

The TMS coil apparatus 100 can be used according to the following method. The cap 300 can be placed on the patient and aligned with respect to the patient's head/facial features. The target marker 310 can be placed on the cap 300 at the desired target for stimulation. An operator can, using the vertical and horizontal axis lasers 180, 182, orient the TMS coil apparatus to get a zero-degree reference orientation from which the forty-five degree orientation from the mid-sagittal plane is determined. The operator can then rotate the TMS coil apparatus to the desired forty-five degree orientation. Then, the operator can, using feedback from the display 230 showing engagement between the contact pads 110 and the target marker 310, position the TMS coil apparatus 100 so that the TMS coil apparatus 100 is centered at the target. The operator can then pivot the TMS coil apparatus 100 until it is tangentially aligned with the patient's head, adjusting the position as needed so that the TMS coil is still centered at the target. The operator can begin using the TMS coil to stimulate the target area while using the remote display 400 to continually monitor the orientation and other aspects (e.g., coil temperature) from a remote location.

In some embodiments, the TMS coil apparatus 100 and, in particular, the array of contact pads 110 and target marker 310, can be used to identify a target area such as a motor hotspot. A motor hotspot can be an area over the patient's motor cortex. Conventionally, the TMS intensity is varied until it reliably stimulates a twitch of the patient's contralateral abductor pollicus brevis muscle. This can be a time-consuming process. By marking the hotspot with the target marker 310, the motor threshold can be assessed quickly and reliably.

Computing Device

Figure 13:
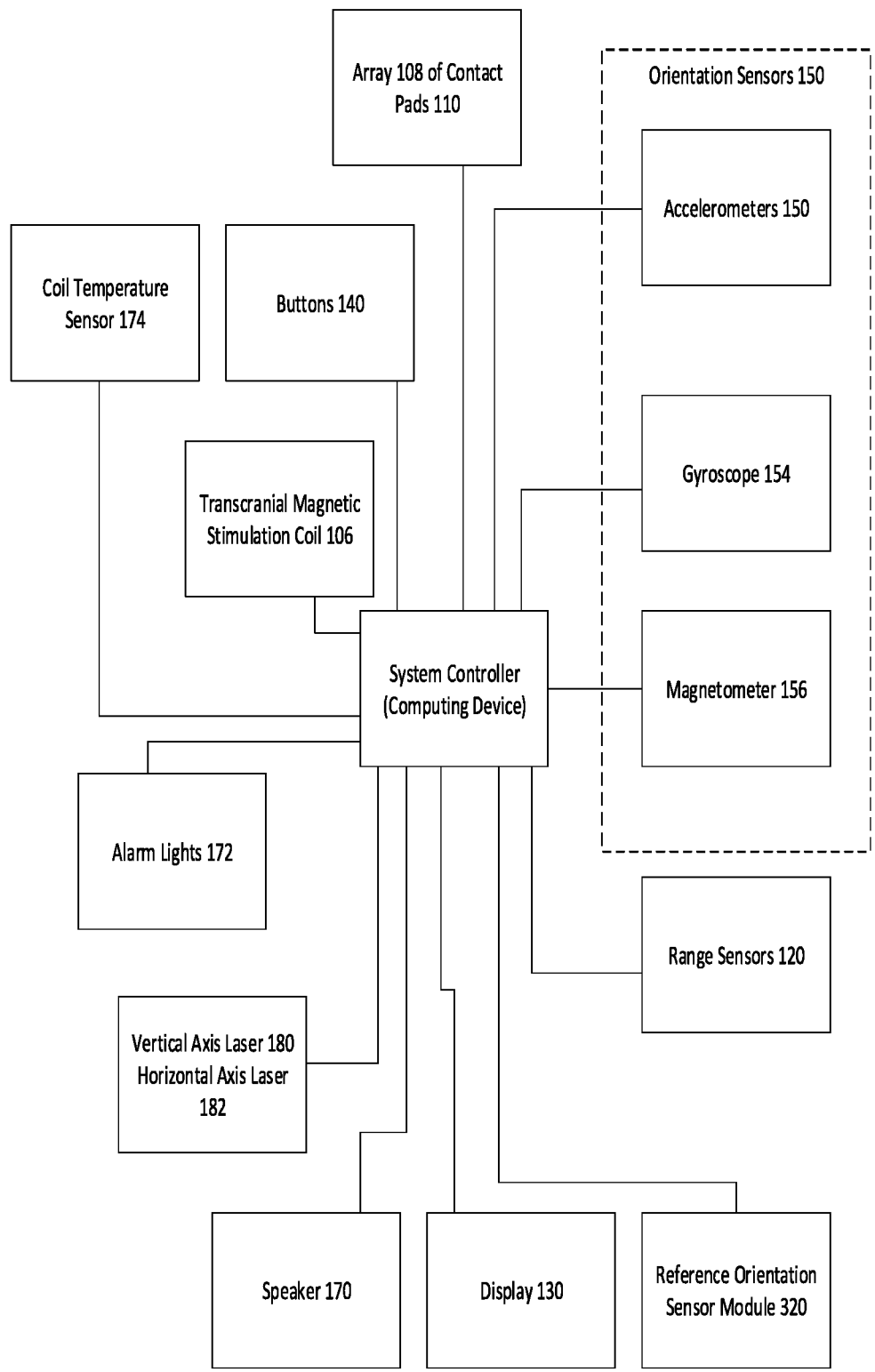
FIG. 13 illustrates an example schematic of components of the TMS coil apparatus as in FIG. 4.
Figure 14:
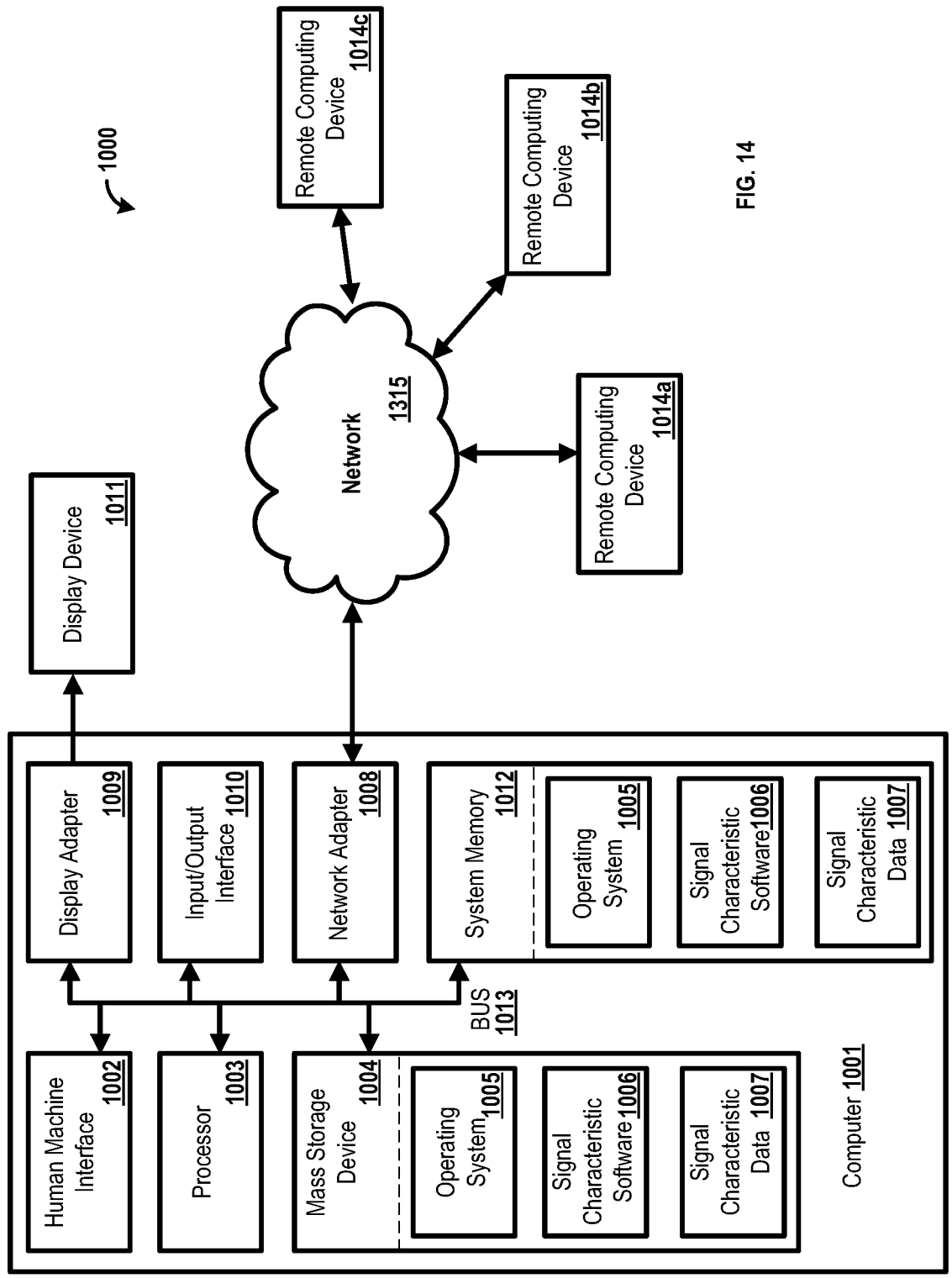
FIG. 14 illustrates an example system including a computing device for the TMS coil apparatus as in FIG. 4.

FIG. 13 illustrates a schematic of the TMS coil apparatus 100 and its components in communication with the controller/computing device 1001. FIG. 14 shows a system 1000 including a computing device 1001 for use with the TMS coil apparatus 100.

The computing device 1001 may comprise one or more processors 1003, a system memory 1012, and a bus 1013 that couples various components of the computing device 1001 including the one or more processors 1003 to the system memory 1012. In the case of multiple processors 1003, the computing device 1001 may utilize parallel computing.

The bus 1013 may comprise one or more of several possible types of bus structures, such as a memory bus, memory controller, a peripheral bus, an accelerated graphics port, and a processor or local bus using any of a variety of bus architectures.

The computing device 1001 may operate on and/or comprise a variety of computer readable media (e.g., non-transitory). Computer readable media may be any available media that is accessible by the computing device 1001 and comprises, non-transitory, volatile and/or non-volatile media, removable and non-removable media. The system memory 1012 has computer readable media in the form of volatile memory, such as random access memory (RAM), and/or non-volatile memory, such as read only memory (ROM). The system memory 1012 may store data such as orientation data 1007 and/or program modules such as operating system 1005 and orientation display software 1006 that are accessible to and/or are operated on by the one or more processors 1003.

The computing device 1001 may also comprise other removable/non-removable, volatile/non-volatile computer storage media. The mass storage device 1004 may provide non-volatile storage of computer code, computer readable instructions, data structures, program modules, and other data for the computing device 1001. The mass storage device 1004 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules may be stored on the mass storage device 1004. An operating system 1005 and orientation display software 1006 may be stored on the mass storage device 1004. One or more of the operating system 1005 and orientation software 1006 (or some combination thereof) may comprise program modules and the orientation display software 1006. Orientation data 1007 may also be stored on the mass storage device 1004. Orientation data 1007 may be stored in any one or more databases known in the art. The databases may be centralized or distributed across multiple locations within the network 1015.

A user (e.g., the clinician) may enter commands and information into the computing device 1001 via an input device (not shown). Such input devices comprise, but are not limited to, a keyboard, pointing device (e.g., a computer mouse, remote control), a microphone, a joystick, a scanner, tactile input devices such as gloves, and other body coverings, motion sensor, and the like. These and other input devices may be connected to the one or more processors 1003 via a human machine interface 1002 that is coupled to the bus 1013, but may be connected by other interface and bus structures, such as a parallel port, game port, an IEEE 1394 Port (also known as a Firewire port), a serial port, network adapter 1008, and/or a universal serial bus (USB).

A display device 1011 may also be connected to the bus 1013 via an interface, such as a display adapter 1009. It is contemplated that the computing device 1001 may have more than one display adapter 1009 and the computing device 1001 may have more than one display device 1011. A display device 1011 may be a monitor, an LCD (Liquid Crystal Display), light emitting diode (LED) display, television, smart lens, smart glass, and/or a projector. In addition to the display device 1011, other output peripheral devices may comprise components such as speakers (not shown) and a printer (not shown) which may be connected to the computing device 1001 via Input/Output Interface 1010. Any step and/or result of the methods may be output (or caused to be output) in any form to an output device. Such output may be any form of visual representation, including, but not limited to, textual, graphical, animation, audio, tactile, and the like. The display 1011 and computing device 1001 may be part of one device, or separate devices.

The computing device 1001 may operate in a networked environment using logical connections to one or more remote computing devices 1014a,b,c. A remote computing device 1014a,b,c may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computing device 1001 and a remote computing device 1014a,b,c may be made via a network 1015, such as a local area network (LAN) and/or a general wide area network (WAN). Such network connections may be through a network adapter 1008. A network adapter 1008 may be implemented in both wired and wireless environments. Such networking environments are conventional and commonplace in dwellings, offices, enterprise-wide computer networks, intranets, and the Internet.

Application programs and other executable program components such as the operating system 1005 are shown herein as discrete blocks, although it is recognized that such programs and components may reside at various times in different storage components of the computing device 1001, and are executed by the one or more processors 1003 of the computing device 1001. An implementation of orientation display software 1006 may be stored on or sent across some form of computer readable media. Any of the disclosed methods may be performed by processor-executable instructions embodied on computer readable media.

In some embodiments, the computing device 1001 may be electronically connected to one or more imaging devices, for example a device or system for performing one or more of computed tomography, radiography, medical resonance imaging, or ultrasound.

EXEMPLARY ASPECTS

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An apparatus comprising: a transcranial magnetic stimulation coil having a central axis; an array of electrical contacts, wherein the array of electrical contacts is configured to contact a conductor on a target area of a target surface; processing circuitry configured to detect an engagement between the conductor and at least two electrical contacts of the array of electrical contacts; a plurality of range sensors spaced from the central axis of the transcranial magnetic simulation coil; and a display configured to display: a location corresponding to the engagement between the conductor and the at least two electrical contacts, distance between each range sensor and the target surface, and angle of coil rotation with respect to a reference position.

Aspect 2: The apparatus of aspect 1, further comprising a first light emitting device configured to display a first line, and a second light emitting device configured to display a second line.

Aspect 3: The apparatus of aspect 2, wherein each of the first light emitting device and the second light emitting device is a laser diode.

Aspect 4: The apparatus of any of the previous aspects 1, further comprising at least one orientation sensor, wherein the processing circuitry is configured to determine an orientation of the transcranial magnetic stimulation coil apparatus based on data from the at least one orientation sensor.

Aspect 5: The apparatus of aspect 4, wherein the at least one orientation sensor comprises a three-axis accelerometer, a three-axis gyroscope, and a three-axis magnetometer.

Aspect 6: The apparatus of aspect 4 or aspect 5, further comprising memory, wherein the processing circuitry is configured to store in the memory a reference orientation based on at least one measurement from the at least one orientation sensor, wherein the processor is configured to determine a relative orientation of the TMS coil with respect to the reference orientation, wherein the display is further configured to display the relative orientation of the TMS coil apparatus with respect to the reference orientation.

Aspect 7; The apparatus of any of the previous aspects, wherein each electrical contact is evenly spaced from each respective adjacent electrical contact.

Aspect 8: The apparatus of any of the previous aspects, wherein the plurality of range sensors comprises at least two range sensors.

Aspect 9: The apparatus of any of the previous aspects, further comprising a wireless transmitter that is configured to transmit data captured by the apparatus to a receiver operably coupled to a remote display.

Aspect 10: The apparatus of any of the previous aspects, wherein the array of electrical contacts is centered with respect to the central axis, and the plurality of range sensors are equally spaced from the central axis.

Aspect 11: The apparatus of any of the previous aspects, wherein the array comprises at least two rows and at least two columns.

Aspect 12: The apparatus of any of the previous aspects, further comprising a second orientation sensor, wherein the processing circuitry is configured to compare orientation data from the second orientation sensor to orientation data from the at least one orientation sensor.

Aspect 13: An apparatus comprising: a housing configured to couple to a transcranial magnetic stimulation coil device; an array of electrical contacts, wherein the array of electrical contacts is configured to contact a conductor on a target area of a target surface; and processing circuitry configured to detect an engagement between the conductor and at least two electrical contacts of the array of electrical contacts; and a plurality of range sensors disposed around a circumference of the array of electrical contacts.

Aspect 14: The apparatus of aspect 13, further comprising a display that is configured to display: a location corresponding to the engagement between the conductor and the at least two electrical contacts, and a distance between each range sensor and the target surface.

Aspect 15: The apparatus of aspect 14, further comprising: at least one orientation sensor, wherein the processing circuitry is configured to determine an orientation of the transcranial magnetic stimulation coil apparatus based on data from the at least one orientation sensor; and memory, wherein the processing circuitry is configured to store in the memory a reference orientation based on at least one measurement from the at least one orientation sensor, wherein the processor is configured to determine a relative orientation of the TMS coil with respect to the reference orientation, wherein the display is further configured to display the relative orientation of the TMS coil apparatus with respect to the reference orientation.

Aspect 16: The apparatus of any of aspects 13-15, further comprising a wireless transmitter that is configured to transmit data captured from the apparatus to a receiver operably coupled to a remote display.

Aspect 17: A system comprising: an apparatus comprising: a transcranial magnetic stimulation coil having a central axis; an array of electrical contacts, wherein the array of electrical contacts is configured to contact a conductor on a target area of a target surface; processing circuitry configured to detect an engagement between the conductor and at least two electrical contacts of the array of electrical contacts; a plurality of range sensors spaced from the central axis of the transcranial magnetic simulation coil; and a wireless transmitter; and a remote display comprising a receiver and that is configured to display: a location corresponding to the engagement between the conductor and the at least two electrical contacts, distance between each range sensor and the target surface, and angle of coil rotation with respect to a reference position, wherein the wireless transmitter is configured to transmit data captured by the apparatus to the receiver of the remote display.

Aspect 18: The system of aspect 17, wherein the apparatus further comprises at least one orientation sensor, wherein the processing circuitry is configured to determine an orientation of the transcranial magnetic stimulation coil apparatus based on data from the at least one orientation sensor, wherein the remote display comprises memory, wherein the processing circuitry is configured to store a reference orientation based on at least one measurement from the at least one orientation sensor, wherein the processor is configured to determine a relative orientation of the TMS coil with respect to the reference orientation, wherein the display is further configured to display the relative orientation of the TMS coil apparatus with respect to the reference orientation.

Aspect 19: A method comprising: receiving a signal corresponding to an engagement between a conductor and at least a first electrical contact and a second electrical contact of a plurality of electrical contacts; determining, based on the signal, a contact location, wherein the contact location is a position between the first electrical contact and the second electrical contact; receiving a distance measurement from each of a plurality of range sensors; displaying the contact location on a display; and displaying the distance measurement from each of the plurality of range sensors on the display.

Aspect 20: The method of aspect 19, wherein displaying the contact location on the display comprises graphically displaying the contact location as a radial offset from a center point.

Aspect 21: The method of aspect 19 or aspect 20, wherein displaying the distance measurement from each of the plurality of range sensors on the display comprises graphically displaying the distance measurement from each of the plurality of range sensors as a radius from a center point.

Aspect 22: The method of any of aspects 19-21, further comprising: calculating a vector as a function of each distance measurement from each of the plurality of range sensors; and displaying the vector on the display.

Aspect 23: The method of any of aspects 19-22, further comprising transmitting the signal and the contact location to the display, wherein the display is a remote display.

Although the foregoing invention has been described in some detail by way of illustration and example for purposes of clarity of understanding, certain changes and modifications may be practiced within the scope of the appended claims.

What is claimed is:

1. An apparatus comprising:
   a transcranial magnetic stimulation (TMS) Coil having a central axis;
   an array of electrical contacts, wherein the array of electrical contacts is configured to contact a conductor on a target area of a target surface;
   processing circuitry configured to detect an engagement between the conductor and at least two electrical contacts of the array of electrical contacts;
   a plurality of range sensors spaced from the central axis of the transcranial magnetic stimulation coil; and
   a display configured to display:
   a location corresponding to the engagement between the conductor and the at least two electrical contacts, and
   a distance between each range sensor and the target surface.

2. The apparatus of claim 1, further comprising a first light emitting device configured to display a first line, and a second light emitting device configured to display a second line.

3. The apparatus of claim 2, wherein each of the first light emitting device and the second light emitting device is a laser diode.

4. The apparatus of claim 1, further comprising at least one orientation sensor, wherein the processing circuitry is configured to determine an orientation of the coil apparatus based on data from the at least one orientation sensor.

5. The apparatus of claim 4, wherein the at least one orientation sensor comprises a three-axis accelerometer, a three-axis gyroscope, and a three-axis magnetometer.

6. The apparatus of claim 4, further comprising memory, wherein the processing circuitry is configured to store in the memory a reference orientation based on at least one measurement from the at least one orientation sensor, wherein the processing circuitry is configured to determine a relative orientation of the TMS coil with respect to the reference orientation, wherein the display is further configured to display the relative orientation of the TMS coil with respect to the reference orientation.

7. apparatus of claim 1, wherein each electrical contact is evenly spaced from each respective adjacent electrical contact.

8. The apparatus of claim 1, wherein the plurality of range sensors comprises at least two range sensors.

9. apparatus of claim 1, further comprising a wireless transmitter that is configured to transmit data captured by the apparatus to a receiver operably coupled to a remote display.

10. The apparatus of claim 1, wherein the array of electrical contacts is centered with respect to the central axis, and the plurality of range sensors are equally spaced from the central axis.

11. The apparatus of claim 1, wherein the array comprises at least two rows and at least two columns.

12. The apparatus of claim 4, further comprising a second orientation sensor, wherein the processing circuitry is configured to compare orientation data from the second orientation sensor to orientation data from the at least one orientation sensor.

13. An apparatus comprising:
a housing configured to couple to a transcranial magnetic stimulation coil device;
an array of electrical contacts, wherein the array of electrical contacts is configured to contact a conductor on a target area of a target surface; and
processing circuitry configured to detect an engagement between the conductor and at least two electrical contacts of the array of electrical contacts; and
a plurality of range sensors disposed around a circumference of the array of electrical contacts.

14. The apparatus of claim 13, further comprising a display that is configured to display:
a location corresponding to the engagement between the conductor and the at least two electrical contacts, and
a distance between each range sensor and the target surface.

15. The apparatus of claim 14, further comprising:
at least one orientation sensor, wherein the processing circuitry is configured to determine an orientation of the transcranial magnetic stimulation coil apparatus based on data from the at least one orientation sensor; and
memory, wherein the processing circuitry is configured to store in the memory a reference orientation based on at least one measurement from the at least one orientation sensor, wherein the processing circuitry is configured to determine a relative orientation of the transcranial magnetic stimulation coil with respect to the reference orientation, wherein the display is further configured to display the relative orientation with respect to the reference orientation.

16. The apparatus of claim 15, further comprising a wireless transmitter that is configured to transmit data captured from the apparatus to a receiver operably coupled to a remote display.

17. A system comprising:
an apparatus comprising:
a transcranial magnetic stimulation coil having a central axis;
an array of electrical contacts, wherein the array of electrical contacts is configured to contact a conductor on a target area of a target surface;
processing circuitry configured to detect an engagement between the conductor and at least two electrical contacts of the array of electrical contacts;
a plurality of range sensors spaced from the central axis of the transcranial magnetic stimulation coil;
a wireless transmitter; and
a remote display comprising a receiver and that is configured to display:
a location corresponding to the engagement between the conductor and the at least two electrical contacts, and
a distance between each range sensor and the target surface,
wherein the wireless transmitter is configured to transmit data captured by the apparatus to the receiver of the remote display.

18. The system of claim 17, wherein the apparatus further comprises at least one orientation sensor, wherein the processing circuitry is configured to determine an orientation of the transcranial magnetic stimulation coil based on data from the at least one orientation sensor, wherein the remote display comprises memory, wherein the processing circuitry is configured to store a reference orientation based on at least one measurement from the at least one orientation sensor, wherein the processing circuitry is configured to determine a relative orientation of the transcranial magnetic stimulation coil with respect to the reference orientation, wherein the display is further configured to display the relative orientation of the transcranial magnetic stimulation coil with respect to the reference orientation.

* * * * *